(12) United States Patent
Ballot-Flurin

(10) Patent No.: US 8,257,747 B2
(45) Date of Patent: Sep. 4, 2012

(54) METHOD TO TREAT PROPOLIS

(75) Inventor: Catherine Ballot-Flurin, Lahitte Toupiere (FR)

(73) Assignee: Ballot-Flurin Apiculteurs, Cauterets (FR)

( * ) Notice: Subject to any disclaimer, the term of this patent is extended or adjusted under 35 U.S.C. 154(b) by 236 days.

(21) Appl. No.: 12/595,149

(22) PCT Filed: Apr. 23, 2008

(86) PCT No.: PCT/FR2008/050736
§ 371 (c)(1),
(2), (4) Date: Jan. 27, 2010

(87) PCT Pub. No.: WO2008/145926
PCT Pub. Date: Dec. 4, 2008

(65) Prior Publication Data
US 2010/0135920 A1    Jun. 3, 2010

(30) Foreign Application Priority Data

Apr. 24, 2007 (FR) .................................. 07 54648

(51) Int. Cl.
*A61K 35/64* (2006.01)
*A61K 8/18* (2006.01)
(52) U.S. Cl. ............ 424/539; 424/49; 424/65; 424/70.1
(58) Field of Classification Search .................. None
See application file for complete search history.

(56) References Cited

FOREIGN PATENT DOCUMENTS

| DE | 43 20 315 A1 | | 12/1994 |
|---|---|---|---|
| DE | 202006012266 U | | 12/2006 |
| EP | 0 109 993 A1 | | 6/1984 |
| FR | 2 374 030 A1 | | 7/1978 |
| FR | 2 594 336 A1 | | 8/1987 |
| FR | 2 837 105 A1 | | 9/2003 |
| JP | 10179057 A | * | 7/1998 |
| KR | 2005004419 A | * | 1/2005 |
| RU | 2105561 C1 | * | 2/1998 |
| WO | WO 02/062362 A2 | | 8/2002 |
| WO | WO 2005/094853 A1 | | 10/2005 |

OTHER PUBLICATIONS

International Search Report, dated Jan. 14, 2009, from corresponding PCT application.
Database WPI Week 198239, Abstract of SU 884 703 B, Nov. 30, 1981, XP-002457214.
Database WPI Week 198701, Abstract of HU 40 010 A, Nov. 28, 2006, XP-002457215.
Database WPI Week 200351, Abstract of JP 2003-061593 A, Mar. 4, 2003, XP-002457216.
Database WPI Week 200604, Abstract of JP 2005-336137 A, Dec. 8, 2005, XP-002457217.
Database WPI Week 199339, Abstract of JP 5-221819 A, Aug. 31, 1993, XP-002457218.
Database CAPLUS, Chemical Abstracts Service, 1911:4349, XP-002457348.
Database EPODOC, European Patent Office, Abstract of JP 8-143462 A, Jun. 4, 1996, XP-002457213.
Database WPI Week 199924, Abstract of JP 10-338641 A, Dec. 22, 1998, XP-002457219.
Database FSTA, International Food Information Service, Abstract of "Antioxidative effect of different kinds of propolis on the oxidation of edible oils" from Korean Journal for Food Science of Animal Resources, 2003, XP-002508303.
Database WPI Week 200538, Abstract of KR 2005 004 419 A, Jan. 12, 2005, XP-002508304.
Database WPI Week 200262, Abstract of RU 2 185 181 C1, Jul. 20, 2002, XP-002508305.
Database WPI Week 198402, Abstract of RO 70 344 A, Jun. 5, 1980, XP-002508306.
Database WPI Week 198307, Abstract of RO 79 518 A, Jul. 30, 1982, XP-002508307.

* cited by examiner

*Primary Examiner* — Qiuwen Mi
(74) *Attorney, Agent, or Firm* — Young & Thompson

(57) ABSTRACT

A method to treat propolis includes conducting at least one first extraction of propolis performed on a batch of raw propolis with a first pure solvent to obtain a first extract having first properties. A second extraction may be performed with a second different pure solvent on the filtration residues obtained after the first extraction, so as to collect and make usable the entirety of the components of propolis using organic solvents only; and finally the method may include a third extraction following after the second extraction, performed on the filtration residues obtained after this second extraction, using a third pure solvent different from the two others; the first solvent then being water, the second being alcohol and the third being oil. The method applies to the production of extracts of propolis for use in the manufacture of hygiene, care, cosmetic products, food products and food supplements.

8 Claims, 5 Drawing Sheets

Alcohol extraction of propolis

4
↓

5 – Make a decoction and mix the filtration residues in alcohol manually and discontinuously for at least 15 days

↓

6 – Collect the filtration residues after one or more filtrations

↓

7 – Collect the alcohol extract

FIG.5

Oil extraction of propolis

7
↓

8 – Macerate the alcohol filtration residues in food oil for at least one week

↓

9 – Collect the filtration residues after one or more filtrations

↓

10 – Collect the oil extract

FIG.6

METHOD TO TREAT PROPOLIS

FIELD OF THE INVENTION

Background of the Invention

The invention concerns a method to treat propolis. It also concerns the extracts of propolis obtained with this method.

The invention applies to the manufacture of hygiene, care, cosmetic, food and food supplement products, comprising one or more propolis extracts obtained with the method.

It is recalled that propolis designates a whole series of resinous, gum and balsamic substances of viscous consistency. These substances are collected on some parts (essentially the buds and bark) of plants (chiefly certain trees) by bees which carry them back to the hive and partly modify them by adding some of their own secretions (essentially wax and saliva secretions).

Propolis is used for numerous purposes inside the hive:
possibly to construct true defense barriers;
to achieve a perfect seal for the hive, allowing good heat insulation;
to varnish all the inner surfaces to eliminate roughness;
to coat new combs and the inside of all the cells with a fine film before the queen comes to lay eggs therein, amounting to efficient disinfection (type of "sterilisation");
finally, to coat, together with wax, all the small animals or insects which cannot be evacuated, a kind of embalming to prevent any putrid decomposition.

It is recognized by the scientific community that propolis is a substance having the following properties:
major antibiotic properties extending to numerous microbial strains, in addition propolis extract increases (potentializes) the efficacy of some antibiotics. Further, experiments have shown that strains of pathogenic microbes are much more sensitive to the action of propolis than of conventional antibiotics: penicillin, tetracycline, ampicillin, monomycin,
antiviral,
antifungal,
anti-germinating,
very powerful anaesthetic properties, much greater inter alia than that of cocaine and additionally does not have its disadvantages with regard to side effects,
notable healing properties through the stimulation of tissue regeneration,
action on neuron metabolism,
antioxidant,
to which must be further added non-negligible anti-inflammatory properties and a favourable influence on some immunological mechanisms which leads to strengthening of pre-disposition against aggressions in general.

Numerous presentations currently exist, of which many in the form of preparations in which propolis is:
either the only active ingredient, in its purified form (i.e. rid of all various mechanical impurities which may have tainted it in the hive: wood fibres, bee hairs, etc.);
or in association (again in its purified form) with other products which are generally medicinal or dietary products.

Therefore, to conclude, at the present time the following is most often found:
propolis in the natural state, purified and the only active ingredient in the form of:
a solid: chewing gum or fragments (of variable size), granules and powder (the latter possibly being in capsules or tablets to be swallowed),
an extract diluted in alcohol: hydroalcoholic solution of propolis in varying concentrations (3 to 30% depending on indications, the average being 15 to 20%),
purified propolis in association with:
various medicinal substances which complete the action of propolis in some particular indications,
ointment or unguent, in which propolis is generally associated with vaseline or lanoline (or both together) in varying percentages generally ranging from 10 to 30% (average of 15%),
dietary products which are most often: honey, pollen or royal jelly or non-apical products (plants),
cosmetics.

SUMMARY OF THE INVENTION

The subject of the present invention is a natural method to treat propolis with which it is possible to obtain a novel presentation of propolis in the form of an extract maintaining all the active components of raw propolis, no solvent mixed with another solvent or with any another product being used for extraction.

A more particular subject of the invention is a natural method to treat propolis, solely using pure biological solvents compatible with organic certification. This method provides several types of extracts, easily soluble and mixable in any type of formula (oil, water, alcohol). The method therefore allows multiple possibilities of application (creams, balsams, dietary preparations), all the types of extract being used as ingredients in comestible products and able to be applied by cutaneous route and ingested by oral route or nasal route.

More particularly, the invention concerns a method to treat propolis consisting of performing at least one first extraction of propolis on a batch of raw propolis with a first pure solvent, to obtain a first extract having first properties.

The method may comprise at least a second extraction performed with a second pure solvent of different type to the first, the extraction with the second solvent being performed on the filtration residues obtained after the extraction performed with the first solvent, so as to collect and make usable all the propolis components, in addition only using organic solvents; and finally, the method may comprise a third extraction following after the second, performed on the filtration residues obtained after this second extraction using a third pure solvent different from the two others; the first solvent then being water, the second being alcohol and the third being oil.

The invention applies to the production of propolis extracts for use in particular in the manufacture of hygiene, care and cosmetic products, food and food supplements.

Therefore, according to a first characteristic, the method to treat propolis comprises an extraction step with a first pure solvent i.e. not mixed with another solvent, performed on a batch of raw propolis to obtain a first extract having first properties.

If the first solvent is water, the extract obtained is an aqueous extract whose properties are antibacterial and isotonic properties i.e. compatible with application to mucosa and applicable directly onto the skin.

According to another characteristic, the extraction of propolis with water is conducted by decoction of propolis, by placing the propolis in water and bringing it to the boil and/or by infusion leaving the propolis to stand in water which has been brought to the boil. Contrary to preconceived opinion, an extract is thereby obtained which has strong activity, the active matter of propolis being maintained.

If the first solvent is alcohol, the extract obtained is an alcohol extract whose properties are antiseptic, antibacterial properties, able to be used in the manufacture of any hygiene or cosmetic product.

Alcohol extraction comprises the following steps:
- 5.1—Raw propolis is left to macerate and is manually mixed discontinuously for at least 15 days,
- 5.2—After one or more filtrations, the filtration residues are collected,
- 5.3—The alcohol extract obtained is collected.

According to another characteristic of the invention, the method comprises a second extraction step with a second pure solvent of different type to the first; extraction with the first solvent being performed on the batch of raw propolis and extraction with the second solvent being conducted on the filtration residues obtained after the extraction conducted with the first solvent, so as to obtain the first propolis extract having first properties then a second extract having second properties, the latter being rid of most impurities.

To obtain a first extract of propolis having isotonic properties i.e. compatible with application to the mucosa (nasal, oral, vaginal) and which can be applied directly to the skin or is able to be consumed, the first solvent is water, the first extract being an aqueous extract, and the second solvent is alcohol, the second extract being an alcohol extract of greater purity (fewer impurities) than existing alcohol extracts.

Alcohol extraction then comprises the following steps:
1—The filtration residues derived from the aqueous extraction step are macerated in alcohol and manually mixed discontinuously for at least 15 days,
2—After one or more filtrations, the filtration residues are collected,
3—The alcohol extract obtained is collected.

For other particular applications, creams, balsams, dietary preparations, therapeutic preparations, the first solvent is alcohol, the first extract being an alcohol extract, the second solvent is oil, the second extract being an oil extract.

In one particularly advantageous embodiment, since it allows a total extract to be obtained i.e. an extract not containing any impurity and containing 100% of the active components of propolis, at least three successive extractions are conducted using solvents of different type, the first solvent is water, the first extract obtained being an aqueous extract, the second solvent is alcohol, the second extract obtained being an alcohol extract, and the third solvent is oil, the third extract being an oil extract, the first extraction being performed on a first batch of propolis and the successive extractions each being performed on the filtration residues obtained after the preceding extraction. With the method, it is therefore possible to collect and to make usable the entirety of the propolis components.

With the treatments of propolis using water as first solvent, and in order to ensure good penetration of the water into the raw propolis, the first step of the method consists of holding the propolis at a temperature of less than zero degrees for a relatively long period, for example 30 days.

The following step is a decoction step of the propolis. The propolis is placed in water brought to the boil and whose temperature is held for sufficiently long time but preferably not exceeding 20 minutes, and the mixture is then left to stand and cool.

Leaving the mixture to stand allows separation of the wax contained in the propolis, and the extract can be collected after one or more filtrations.

The filtration residues are kept for the following extraction(s).

The second extraction comprises maceration in alcohol and daily, discontinuous, manual mixing of the filtration residues obtained after the first extraction for a period of at least fifteen days, followed by one or more filtrations of the extract to obtain the purified alcohol extract and filtration residues.

If three successive extractions are performed, allowing a total extract to be obtained, the first extraction consists of:
Conducting long, aqueous extraction of propolis to obtain an aqueous extract of propolis and filtration residues, holding the propolis at a temperature of less than zero degrees for a relatively long period, for example 30 days, then carrying out decoction of the propolis, the propolis being placed in water brought to the boil for a time not exceeding 20 minutes, and finally leaving it to stand for at least 24 h, the second extraction consists of:
Conducting long, alcohol extraction using the filtration residues obtained after the aqueous extraction, to obtain an alcohol extract of propolis and filtration residues, by macerating the filtration residues in alcohol and mixing manually and discontinuously for at least 15 days, the third extraction consists of:
Conducting long, oil extraction using the residues from the alcohol extraction to obtain an oil extract of propolis and filtration residues, by leaving the residues from alcohol extraction to macerate in oil for at least one week.

The invention applies to the manufacture of hygiene, health, cosmetic, food and food supplement products.

The invention applies to the manufacture of a body deodorant comprising at least 50% of aqueous extract of propolis in its composition, obtained following the method of the present invention.

The invention applies to the manufacture of a nasal hygiene product containing 50% of aqueous extract of propolis in its composition, obtained following the method of the present invention.

The invention applies to the manufacture of an ear hygiene product consisting of 100% aqueous extract of propolis obtained following the method of the present invention.

The invention applies to the manufacture of an intimate hygiene product containing 5% alcohol extract of propolis in its composition, obtained after a second extraction according to the method.

The invention applies to the manufacture of an after-shave care cream comprising a complex of propolis extracts containing 14% oil extract and 10% aqueous extract in its composition obtained following the method.

The invention applies to the manufacture of an anti-oxidant product for the area around the eyes, having a smoothing effect on eyebags and fine lines, comprising a complex of propolis extracts containing 14% oil extract and 10% aqueous extract in its composition obtained using the method of the invention.

The invention applies to the manufacture of an anti-oxidant product for body care having a hydrating and protective effect, comprising a complex of propolis extracts containing 8% propolis oil extract and 12% propolis aqueous extract in its composition, obtained using the method of the invention.

The invention applies to the manufacture of a shower cream for the body, face and hair, containing 1% alcohol extract in its composition obtained following the method according to the invention.

The invention applies to the manufacture of a regenerating care shampoo, containing 2.5% alcohol extract in its composition, obtained using the method according to the invention.

The invention applies to the manufacture of a toothpaste, containing at least 3% alcohol extract of propolis in its composition, obtained using the method according to the invention.

BRIEF DESCRIPTION OF THE DRAWINGS

Other particular aspects and advantages of the invention will become clearly apparent on reading the description given below as a non-limiting, illustrative example with reference to the figures in which.

DETAILED DESCRIPTION OF THE INVENTION

Figure 1:
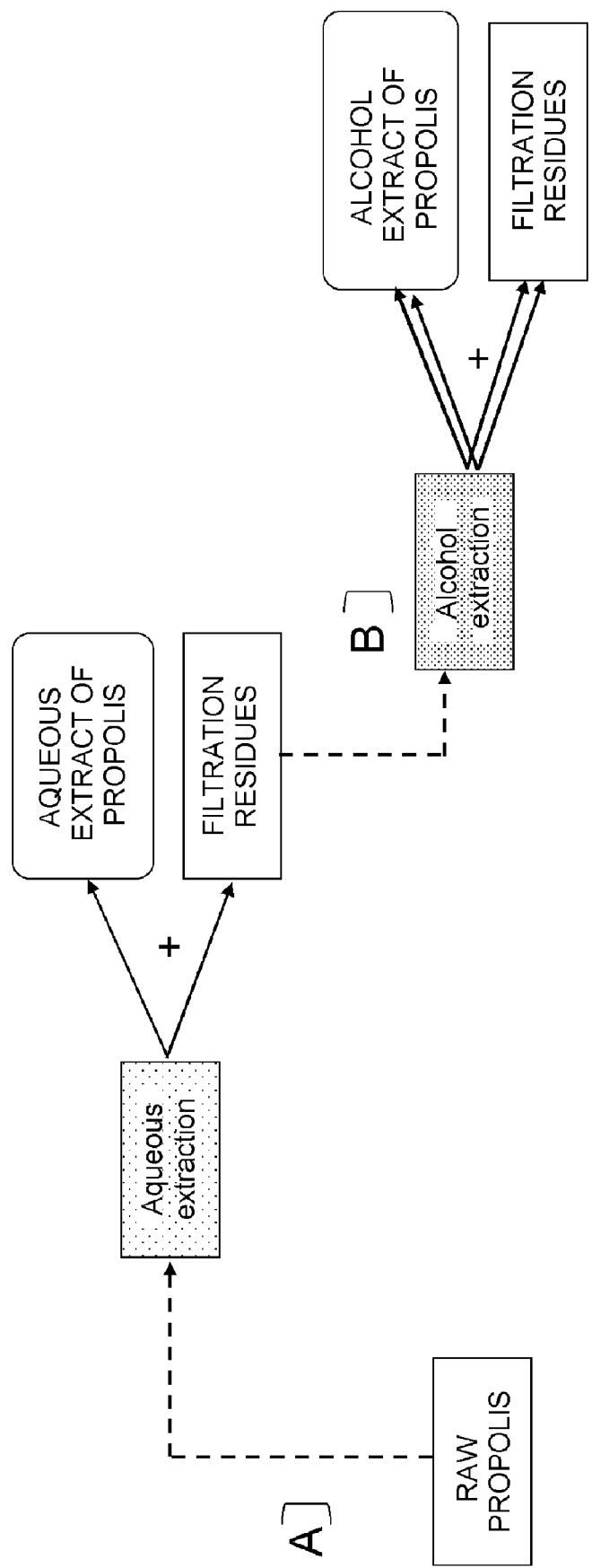
FIG. 1 gives the steps performed according to the method of the invention in a first embodiment, FIG. 2 gives the steps performed according to the method of the invention in a second embodiment, FIG. 3 gives the steps performed according to the method of the invention in a third embodiment, FIG. 4 gives the detailed steps of an aqueous extraction according to the invention, FIG. 5 gives the steps of an alcohol extraction according to the invention, FIG. 6 gives the steps of an oil extraction according to the invention.
Figure 2:
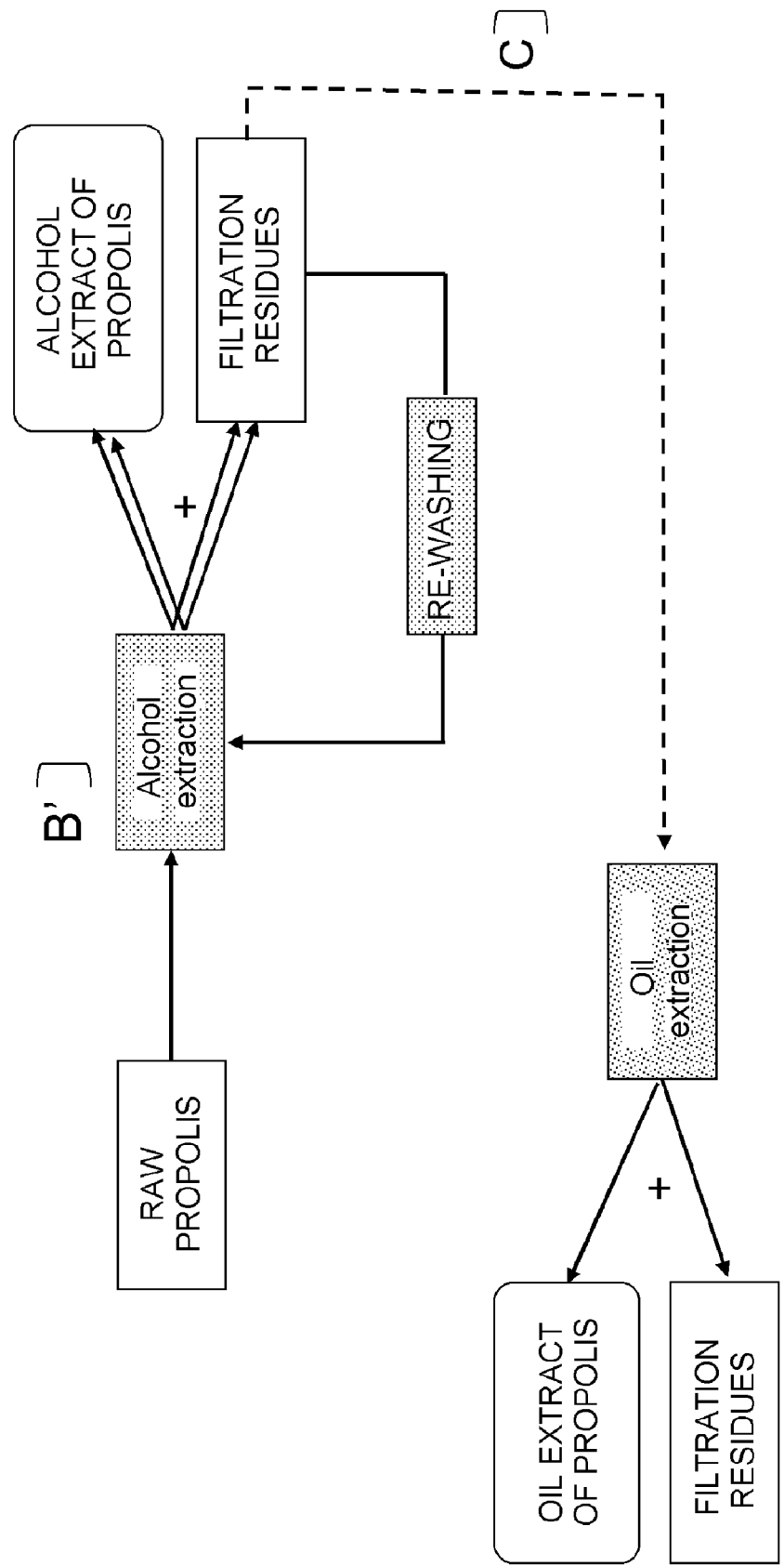
Figure 3:
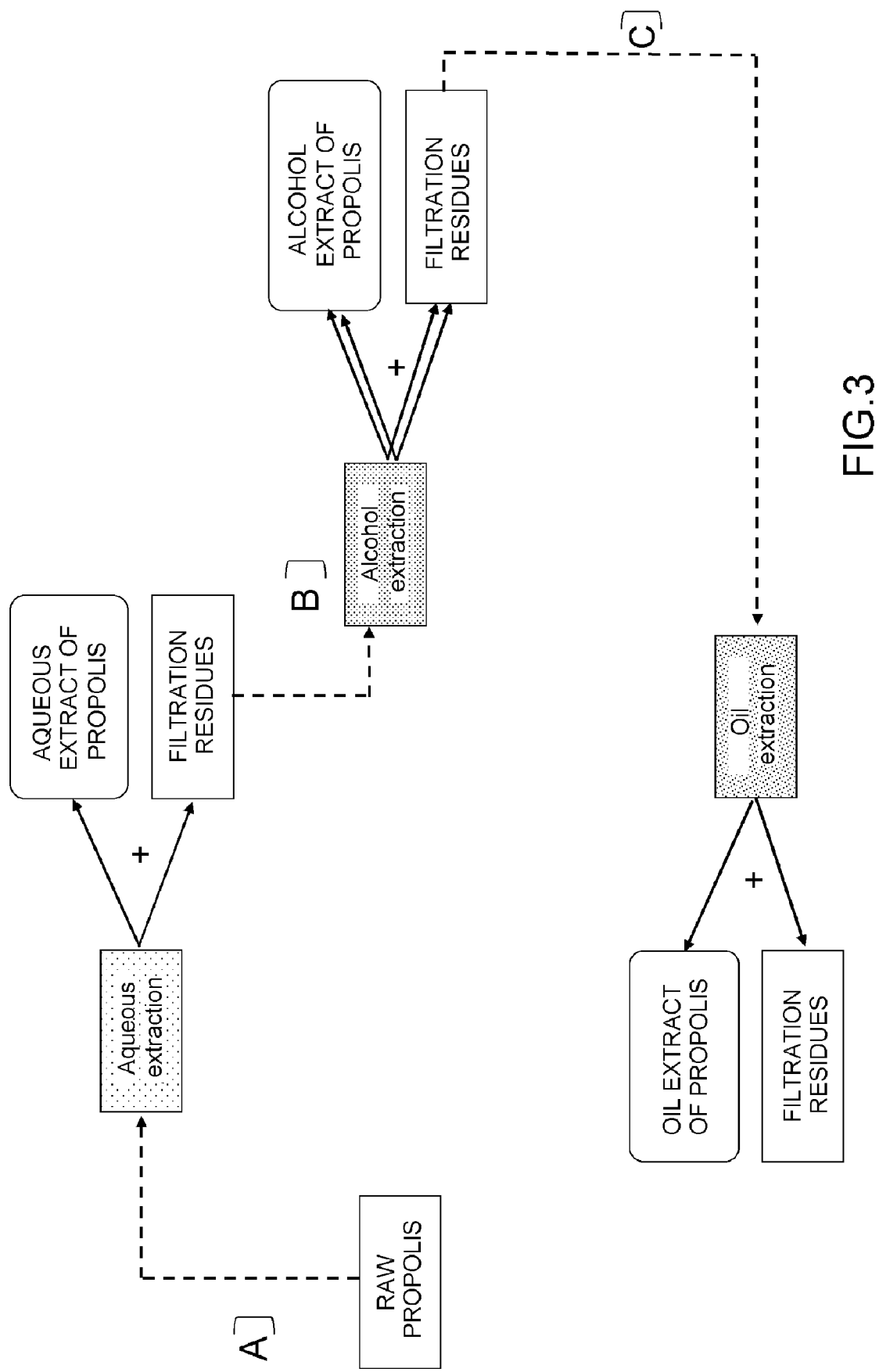

With the method of the invention, it is possible to obtain two or three extracts of different type (aqueous, alcohol and oil) which may be used for different applications.

With the method, it is further possible, after each extraction, to obtain different active components of propolis. The advantage provided by extraction with water followed by extraction with alcohol, is that water extraction only removes active materials that are non-soluble in alcohol, and water vapour facilitates the dissolving in alcohol of alcohol-soluble active components. Similarly, by performing extraction with alcohol and then with oil, no impurity is obtained (100% purity) and 100% active components.

For this purpose, the method comprises the conducting of one or two or three successive extractions performed on one same batch of raw propolis (raw propolis for the first extraction) and on the residues obtained after the preceding extractions of propolis for the other one or two extractions. If several extractions of propolis are conducted in sequence, they are not performed on separate batches.

Also, the extractions performed are long extractions (long in time, or slow) as compared with current practice which consists of conducting an extraction within a few hours. This slow conducting and the absence of machines allows the subtle elements to mutate better and avoids deterioration of the physical structure of propolis.

According to a first characteristic of the invention, the method consists of performing an extraction with a first pure solvent i.e. a solvent not mixed with another solvent. This extraction is performed on a batch of raw propolis to obtain a first extract having first properties.

For particular applications, the method goes against preconceived ideas since the solvent is water without any other solvent or additive. With the method, it is therefore possible to obtain an aqueous extract which has the active materials of propolis, imparting to it antiseptic, antibacterial and isotonic properties. The applications are for example the manufacture of deodorants, nasal or ear hygiene products.

The aqueous extract is conducted by decoction of the propolis. The propolis is placed in water and it is brought to the boil. This extract can be obtained by infusing i.e. by leaving the propolis to stand in water which has been brought to the boil. It is also possible to conduct decoction and then to leave the propolis to stand in water brought to the boil (infusion).

For other applications, the pure solvent is alcohol; the extract obtained is an alcohol extract whose properties are antiseptic, antibacterial properties.

According to another characteristic of the invention, the method comprises a second extraction of propolis with a second pure solvent of different type to the first. Extraction with the first solvent is performed on the batch of raw propolis, and extraction with the second solvent is performed on the filtration residues obtained after the extraction with the first solvent, so as to obtain the first extract of propolis having first properties then a second extract having second properties, this latter being rid of most of the impurities.

In a first embodiment, the first solvent is water and the second solvent is alcohol.

In this first embodiment allowing an aqueous extract and an alcohol extract to be obtained from one batch of propolis, the following operations are carried out:

A] Long, Aqueous Extraction:
1—The propolis is held at a temperature of less than zero degrees for a relatively long period, for example 30 days,
2—Decoction of the propolis: the propolis is placed in water and brought to the boil for a time not exceeding 20 minutes, then it is left to stand for at least 24 h,
3—The extract is collected. This collection is made after one or more filtrations.
4—The filtration residues are collected.

B] Long, alcohol extraction: The residues obtained after step 4 are used to perform alcohol extraction according to the scheme in FIG. 5.
5—The filtration residues are left to macerate in alcohol, and are mixed manually and discontinuously for at least 15 days,
6—The filtration residues are collected after one or more filtrations,
7—The alcohol extract obtained is collected.

Second embodiment: treatment of a batch of propolis, the first solvent is alcohol and the second solvent is oil.

B'] Long, alcohol extraction: Steps 5 to 7 just described are implemented, however the treatment is started with raw propolis, step 5 is therefore performed on raw propolis and not on filtration residues.
5.1—The raw propolis is left to macerate and is manually mixed discontinuously for at least 15 days,
5.2—After one or more filtrations, the filtration residues are collected,
5.3—The alcohol extract obtained is collected.

C] Oil Extraction:
8—The filtration residues collected after step 5.2 are left to macerate in food oil held at constant temperature for at least one week, preferably for one to four weeks,
9—Filtering or decanting is performed,
10—The oil extract obtained is collected.

According to another characteristic of the method, three successive extractions are performed.

In this case, the successive conducting is performed of an aqueous extraction, then an alcohol extraction, then an oil extraction using one same batch of raw propolis.

Figure 4:
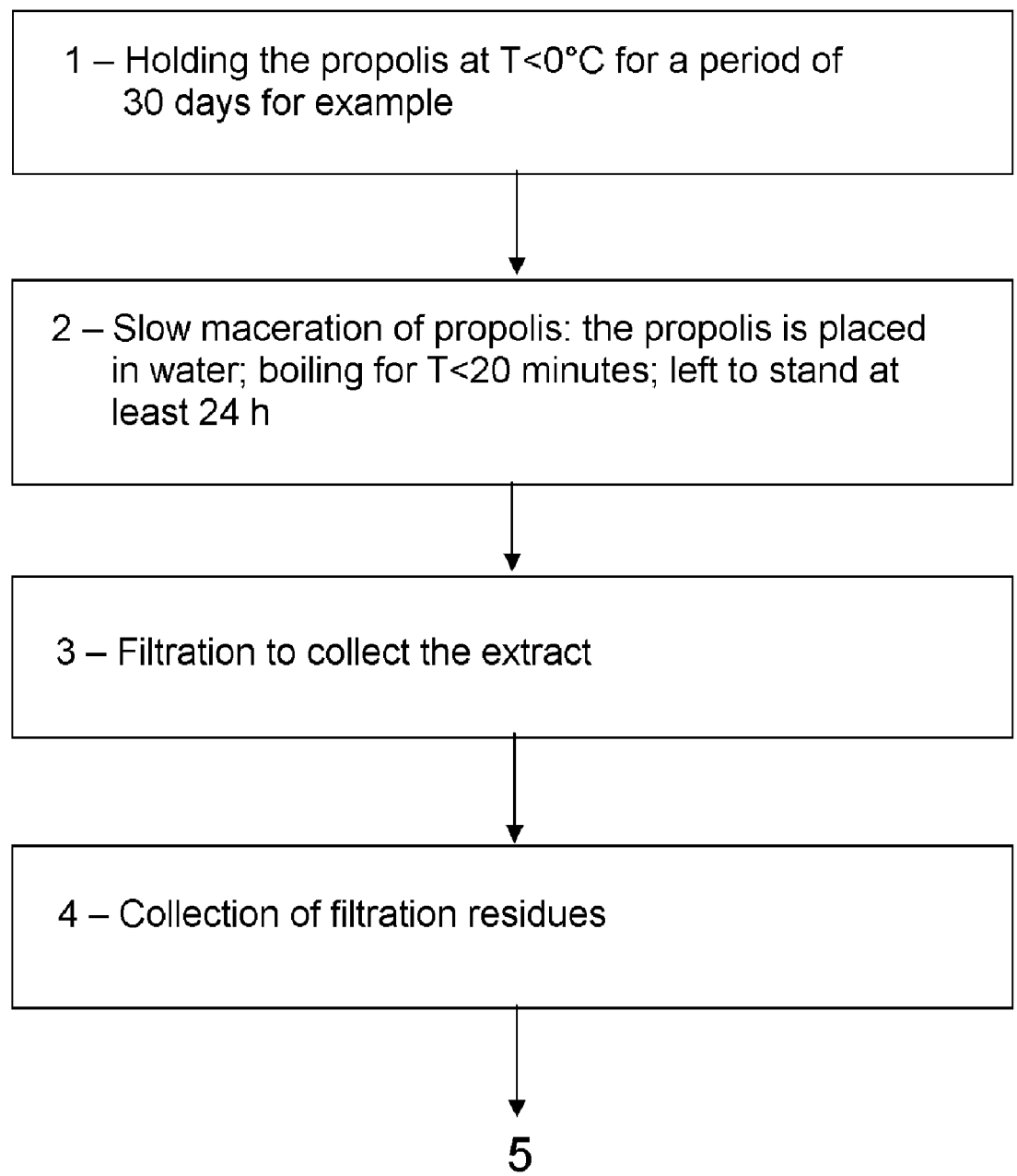

In one particular embodiment, the following steps are carried out:

A) Long, Aqueous Extraction (FIG. 4):
1—Holding the raw propolis at a temperature of less than zero degrees for a relatively long time, for example 30 days,
2—Decoction of the propolis: the propolis is placed in water and brought to the boil for a time not exceeding 20 minutes,
3—This is left to stand for at least 24 h to collect the extract. This collection is conducted after one or more filtrations,
4—The filtration residues are collected.

B) Long, Alcohol Extraction (FIG. 5):
The residues derived from step 4 are used to perform alcohol extraction following the scheme in FIG. 5.
5—The filtration residues are left to macerate in alcohol and are manually mixed discontinuously for at least 15 days,
6—After one or more filtrations, the filtration residues are collected,
7—The alcohol extract obtained is collected.

C] Oil Extraction (FIG. 6):
8—The filtration residues collected after step 6 are left to macerate in oil,
9—Filtration or decanting is conducted,
10—The oil extract obtained is collected.

With the present invention, it is therefore possible to obtain an aqueous extract, an alcohol extract and an oil extract—each extract can be used independently or associated with another for the production of hygiene, health or cosmetic products, food products or food supplements.

Some examples of application are given below. These applications were the subject of laboratory tests confirming the stated properties and tolerance by the human body.

Applications of extracts of propolis and of complexes of propolis extracts obtained following the method described above:

1—Body Deodorant (Armpits, Chest, Moist Feet and Hands, and Intimate Areas) which the Applicant Calls: DEODORANT UNIVERSEL BIS.

Composition: 99.9% aqueous extract of organic propolis and 0.1% elixir marketed by the applicant under the name Elixir de la Ruche Sueur du Ciel.

Different studies were carried out by Institut Dermatologique d'Aquitaine on the above formula, targeting the evaluation of:
a—cosmetic acceptability
b—gynaecological tolerance under the supervision of a gynaecologist,
c—Skin tolerance under the supervision of a dermatologist.

Conclusions of the study report show that:
The formula has:
good global cutaneous tolerance;
satisfactory cosmetic acceptability;
good skin-mucosal tolerance.
d—bactericidal action on the strains:
d1—*Corynebacterium xerosis*
d2—*Staphylococcus epidermidis*
d3—*Propionibacterium acnes*

2—Intimate Hygiene with High Tolerance, which the Applicant Calls: PAIN HYGIÈNE INTIME, Composition: 94% organic soap batter of plant origin (commercially available), organic honey (commercially available), 5% alcohol extract of organic propolis obtained following the method, 1% elixir marketed by the applicant under the name Élixir de la Ruche Vol Nuptial.

Different studies were carried out by Institut Dermatologique d'Aquitaine on the above formula.

a—Evaluation of skin tolerance after a single application covered by an occlusive dressing for 48 hours under the supervision of a dermatologist.

Conclusion of the study report: the PAIN HYGIENE INTIME applied in a 2% solution can be considered to be non irritant after 48 hours' consecutive application under an occlusive dressing in 11 volunteers.

b—Evaluation of gynaecological tolerance and of cosmetic qualities after 21 days' application under the supervision of a gynaecologist.

Conclusions of the study report: the PAIN HYIÈNE INTIME has good global skin-mucosal tolerance and good cosmetic acceptability.

3—Soothing after-Shave Care-Micro-Cuts-Natural Healing

Product called: CRÈME DE FORCE by the applicant.

Composition: emulsion (76% aqueous or oil base) prepared with a complex of propolis extracts: 14% oil extract and 10% aqueous extract of propolis.

Different studies are in progress by Institut Dermatologique d'Aquitaine on the above formula with a view to confirming:

The above-cited properties (soothing after-shave care-micro-cuts-natural healing).
skin tolerance after a single application under an occlusive dressing for 48 hours.
skin tolerance and cosmetic qualities after 21 days of application.
Eye tolerance.

4—Antioxidant—Smoothes Eye Bags and Fine Lines
Product called: YEUX DE REINE by the applicant.
Composition: emulsion (76% aqueous or oil base) prepared with a complex of propolis extracts: 14% oil extract and 10% aqueous extract of propolis.

The above-cited properties (antioxidant—smoothes eye bags and fine lines).
Skin tolerance after a single application under an occlusive dressing for 48 hours.
Skin tolerance and cosmetic qualities after 21 days' application.
Eye tolerance.

5—Antioxidant—Hydrating and Protective
Product called: LAIT DE RUCHE by the applicant.
Composition: emulsion (80% aqueous or oil base) prepared with a complex of propolis extracts: 8% oil extract and 12% aqueous extract of propolis.

Different studies are in progress by Institut Dermatologique d'Aquitaine on the above formulas with a view to confirming:

The above-cited properties (antioxidant-hydration-protection).
Skin tolerance after a single application under an occlusive dressing for 48 hours,
Skin tolerance and cosmetic qualities after 21 days' application.

6—Healthy Scalp
Itchy scalp,
Scalp cleansing,
Anti-dandruff,
Anti-hair loss—alopecia
→for healthy reinvigorated hair.
Product called: CRÈME DOUCHE DE LA RUCHE by the applicant
Composition: 94% cleansing base of plant origin, 1% alcohol extract of propolis, 5% honey.

Product called: SHAMPOING DOUCHE ASSAINISSANT ET DOUR by the applicant.

Composition: 94% cleansing base of plant origin, 1% alcohol extract of propolis, 5% honey Product called: SHAMPOING SOIN RÉGÉNÉRANT by the applicant.

Composition: 97.5% cleansing base of plant origin, 2.5% alcohol extract of propolis 7—Nose and Ear Hygiene Nasal Application Allergies and seasonal sensitivity—antiviral action Cleansing of pollution residues Hydration of nasal mucosa.

Product called: SPRAY NASAL DES PYRÉNÉES by the applicant.

Composition: isotonic preparation containing 50% plant extracts and 50% aqueous extract of propolis.

Ear Application

Soothing, cleansing, anti-itch ear bath.

Product called EXTRAIT DE PROPOLIS SANS ALCOHOL by the applicant (alcohol-free extract).

Composition: isotonic preparation containing 100% aqueous extract of propolis.

8—Dental and Mouth Hygiene

Natural whitening through anti-bacterial effect,

Parodontosis,

Cleansing of contours of dental implants and prostheses.

Product called: DENTIFRICE SOURIRE by the applicant.

Composition: preparation containing 3.1% alcohol extract of propolis and 96.9% of a basic hygiene product for teeth, available commercially.

Different studies have been conducted by Institut Dermatologique d'Aquitaine on the above formula, including evaluation of tolerance and acceptability after 21 days' application under the supervision of a stomatologist.

Conclusions of the study report: the formula shows very good stomatological tolerance and good cosmetic acceptability.

The invention claimed is:

1. A method to treat propolis, comprising:
    A) an aqueous extraction comprising extracting raw propolis with a pure water solvent and filtering to obtain (i) a first filtration residue and (ii) an aqueous extract having antibacterial, antiseptic and isotonic properties that are compatible with application to mucosa and directly applicable to the skin;
    B) an alcohol extraction comprising extracting the first filtration residue with a pure alcohol solvent and filtering to obtain (iii) a second filtration residue and (iv) an alcohol extract having antiseptic and antibacterial properties; and
    C) an oil extraction comprising extracting the second filtration residue with a pure oil solvent and filtering to obtain (v) an oil extract.

2. The method to treat propolis according to claim 1, wherein the A) aqueous extraction comprises:
    decocting the propolis by placing the propolis in water, bringing the water to a boil and/or by infusion, and leaving the propolis to stand in the water brought to a boil.

3. The method according to claim 1, wherein the A) aqueous extraction comprises:
    holding the raw propolis at a temperature below 0° C. for a period of several days,
    decocting the propolis by placing the propolis in water, bringing the water to a boil for a time not exceeding 20 minutes, and then leaving to stand for at least 24 hours,
    filtering and collecting the aqueous extract and the first filtration residue.

4. The method according to claim 1, wherein the B) alcohol extraction comprises:
    macerating the first filtration residue in the alcohol and discontinuously mixing for at least 15 days, and
    filtering and collecting the alcohol extract and the second filtration residue.

5. The method according to claim 1, wherein,
    A) the aqueous extraction comprises:
        holding the raw propolis at a temperature of less than 0° C. for a period of several days,
        decocting the propolis by placing the propolis in water, bringing the water to a boil for a time not exceeding 20 minutes, and leaving to stand for at least 24 hours, and
        filtering and collecting the aqueous extract and the first filtration residue;
    B) the alcohol extraction comprises:
        macerating the first filtration residue in the alcohol and discontinuously mixing for at least 15 days,
        filtering and collecting the alcohol extract and the second filtration residue; and
    C) the oil extraction comprises:
        macerating the second filtration residue in the oil for at least one week,
        filtering and collecting the oil extract.

6. The method according to claim 3, comprising holding the raw propolis at a temperature below 0° C. for a period of at least 30 days.

7. The method according to claim 4, wherein the discontinuous mixing is performed manually.

8. The method according to claim 5, comprising macerating the second filtration residue in the oil for one to four weeks.

* * * * *